US00PP29038P2

(12) United States Plant Patent
Radler

(10) Patent No.: US PP29,038 P2
(45) Date of Patent: Mar. 6, 2018

(54) SHRUB ROSE PLANT NAMED 'RADGARDEBYEL'

(50) Latin Name: *Rosa hybrida*
Varietal Denomination: Radgardebyel

(71) Applicant: THE CONARD-PYLE COMPANY, West Grove, PA (US)

(72) Inventor: William J. Radler, Greenfield, WI (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 15/330,674

(22) Filed: Oct. 27, 2016

(51) Int. Cl.
*A01H 5/02* (2006.01)

(52) U.S. Cl.
USPC ..... Plt./104

(58) Field of Classification Search
USPC ..... Plt./101, 102, 104
See application file for complete search history.

(56) References Cited

U.S. PATENT DOCUMENTS

PP13,063 P2 10/2002 Radler

*Primary Examiner* — Susan McCormick Ewoldt
*Assistant Examiner* — Karen M Redden
(74) *Attorney, Agent, or Firm* — Buchanan Ingersoll & Rooney PC

(57) ABSTRACT

A new and distinct variety of shrub rose plant herein referred to by its cultivar name, 'Radgardebyel', is provided which forms in abundance on a substantially continuous basis attractive, cup-shaped, yellow colored blossoms. The vegetation is vigorous and the growth habit is very bushy and rounded. Attractive, semi-glossy, medium green foliage is formed. Very good disease resistance is exhibited, particularly for black spot, rust, and mildews. Additionally, the new variety is particularly well suited for growing as distinctive ornamentation in the landscape.

1 Drawing Sheet

Botanical/commercial classification: *Rosa hybrida*/Shrub Rose Plant.

Varietal denomination: cv. Radgardebyel.

SUMMARY OF THE INVENTION

The new variety of shrub rose plant of the present invention was created by controlled breeding in June of 2007 in Greenfield, Wis., U.S.A., by artificial pollination wherein two parents were crossed which previously had been studied in the hope that they would contribute the desired characteristics. The female parent (i.e., the seed parent) of the new variety was the 'Radgold' (non-patented) variety. The male parent (i.e., the pollen parent) of the new variety was the 'Radgemmis' (non-patented) variety. The parentage of the new variety can be summarized as follows:

'Radgold'×'Radgemmis'.

The seeds resulting from the above pollination were sown and small plants were obtained which were physically and biologically different from each other. Selective study resulted in the identification of a single plant of the new variety.

It was found that the new shrub rose plant of the present invention possesses the following combination of characteristics:

(a) abundantly and substantially continuously forms attractive, cup-shaped, yellow colored blossoms,
(b) exhibits a very bushy and rounded growth habit,
(c) forms vigorous vegetation,
(d) forms attractive, ornamental, semi-glossy, medium green foliage, (e) exhibits very good disease resistance, particularly with respect to black spot, rust, and mildews, and
(f) is well suited for providing attractive ornamentation.

A new rose variety is provided displaying attractive, cup-shaped, yellow colored blossoms combined with substantially continuous blossoming and very good disease resistance.

The new variety well meets the needs of the horticultural industry. It can be grown to advantage as ornamentation in parks, gardens, public areas, and in residential landscapes. Accordingly, the plant is particularly well suited for growing in the landscape.

The new variety of the present invention can be readily distinguished from the seed parental variety, 'Radgold' (non-patented), in that the new variety displays petals that are yellow in coloration rather than gold, as in the parent, and displays better color retention than the parent.

The present invention can be readily distinguished from the pollen parent, 'Radgemmis' (non-patented), in that the new variety has an improved, more rounded habit, better foliage, and better productivity than 'Radgemmis'.

The new variety of the present invention can be readily distinguished from other rose varieties such as 'Radsun' (U.S. Plant Pat. No. 13,063) in that the new variety exhibits blooms with a smaller diameter than the blooms of 'Radsun'.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radgardebyel', and will be marketed under the CHAMPION YELLOW Trademark.

BRIEF DESCRIPTION OF THE PHOTOGRAPHS

The accompanying photograph shows, as nearly true as it is reasonably possible to make the same in a color illustration of this character, typical blossoms of the new variety. The rose plant of the new variety illustrated herein was approximately three years of age and was grown outdoors on its own roots in West Grove, Pa., U.S.A. when it was observed in June 2015.

FIG. 1 shows close view of the blossoms and foliage of the new variety.

DETAILED BOTANICAL DESCRIPTION

The chart used in the identification of colors is that of The Royal Horticultural Society (R.H.S. Colour Chart—2015 Edition), London, England. The description is based on the observation of three-year-old specimens of the new variety during June while growing in ground on their own roots at West Grove, Pa., U.S.A.

Class: Shrub Rose.

*Variety*.—'Radgardebyel'.

Plant:

*Height*.—Commonly up to approximately 91 cm on average.

*Width*.—Commonly up to approximately 61 cm on average.

*Habit*.—Very bushy and rounded.

Stems:

*Length*.—Main stems commonly approximately 50 cm on average, and secondary stems commonly approximately 20 cm on average.

*Color*.—Near Yellow-Green Group 146C mixed with Greyed-Orange Group 176A on young stems, and commonly near Yellow-Green Group 146B on old wood.

*Thorns*.—Size: commonly approximately 1 cm in length on average and approximately 4 mm in width on average at the point of attachment when young, and approximately 1.5 cm in length on average and approximately 1 cm in width on average at the point of attachment when old. Color: commonly near Yellow-Green Group 153A on young stems, and near Greyed-Red Group 182A when old.

Leaves:

*Size*.—Commonly approximately 12.5 cm in length on average, and approximately 10 cm in width on average for a five-leaflet leaf.

*Leaflets*.—Number: 3, 5, and 7. Length: approximately 5.5 cm on average for a terminal leaflet, and approximately 3.2 cm on average for a lower leaflet. Width: approximately 4 cm on average for a terminal leaflet, and approximately 1.3 cm on average for a lower leaflet. Shape: generally ovate. Margins: serrate. Texture: generally smooth on the upper and under surfaces. Color: (when young): Upper surface: near Yellow-Green Group 146A. Under surface: near Yellow-Green Group 146A blended with Greyed-Red group 178A. Color (when fully mature): Upper surface: near Green Group NN137A. Under surface: near Green Group 147B.

Inflorescence:

*Number of flowers*.—Commonly in a cluster of approximately 1 to 4 blossoms on average per stem, and commonly with approximately 50-60 blossoms on average being present on the plant at a given time.

*Peduncle*.—Near Yellow-Green Group 144A overlaid with Red-Purple Group 60A in coloration, commonly approximately 2 cm in length on average, approximately 3 mm in diameter on average, and commonly sparsely covered with small flexible thorns less than 2 mm in length.

*Sepals*.—Upper surface: covered with short pubescence, and commonly near Green Group 138B in coloration. Under surface: commonly puberulent, and commonly near Yellow-Green Group 144A in coloration. Size: commonly approximately 2.5 cm in length on average, and approximately 8 mm in width at the base. Margin: entire, and commonly with an extension on three of the sepals measuring approximately 6 mm in length on average and approximately 1.5 mm in width on average. Number: five.

*Buds*.—Shape: generally ovoid. Length: approximately 1.5 cm on average. Diameter: approximately 1 cm on average. Color: when opening, near Yellow Group 7A.

*Flower*.—Form: semi-double, cuplike. Diameter: commonly approximately 5 cm on average when fully open. Color (when opening begins): Upper and under surface: near Yellow Group 5A at the point of attachment transitioning to near Yellow Group 4B moving toward the apex. Color (at end of blooming): Upper surface: near Yellow Group 5B at the point of attachment transitioning to near Yellow Group 11D towards the apex with a hint of Orange Group 27C at the margin. Under surface: near Yellow Group 5B at the point of attachment transitioning to near Yellow Group 11D towards the apex. Fragrance: slight. Petal number: commonly approximately 15 on average under normal growing conditions. Petal length: commonly approximately 3.3 cm on average. Petal width: commonly approximately 3.5 cm on average. petal shape: broadly obovate. Petal margin: entire. Petal apex shape: rounded. Petal base shape: cuneate. Margin: entire. Petal drop: good, the petals commonly detach cleanly and freely drop upon full maturity. Stamen number: approximately 96 on average. Anthers: number approximately 96 on average and commonly near Yellow-Orange Group 15A in coloration. Filaments: approximately 8 mm in length, and the coloration is near Yellow Group 13A. Pollen: commonly present in an abundant quantity, and near Orange Group 25A in coloration. Pistils: separate and free, and commonly number approximately 25 on average. Styles: commonly approximately 3 mm in length and near Red Group 47C. Stigma: commonly approximately 1 mm in diameter on average, and near Orange Group 15B in coloration. Receptacle: commonly substantially round in shape, approximately 7 mm in diameter, smooth in texture, near Yellow-Green Group 144A in coloration, and with achenes commonly being present on the bottom and wall.

Development:

*Vegetation*.—Medium green, vigorous, and strong.

*Blossoming*.—Abundant and substantially continuous from spring to frost.

*Resistance to diseases*.—Very good resistance, particularly with respect to black spot, rust, and mildews.

Plants of the 'Radgardebyel' variety have not been observed under all possible environmental conditions to date. Accordingly, it is possible that the phenotypic expression may vary somewhat with changes in light intensity and duration, cultural practices, and other environmental conditions.

I claim:

1. A new and distinct rose plant characterized by the following combination of characteristics:

(a) abundantly and substantially continuously forms attractive, cup-shaped, yellow colored blossoms, (b) exhibits a very bushy and rounded growth habit, (c) forms vigorous vegetation, (d) forms attractive, ornamental, semi-glossy, medium green foliage, (e) exhibits very good disease resistance, particularly with respect to black spot, rust, and mildews, and (f) is well suited for providing attractive ornamentation, substantially as herein shown and described.

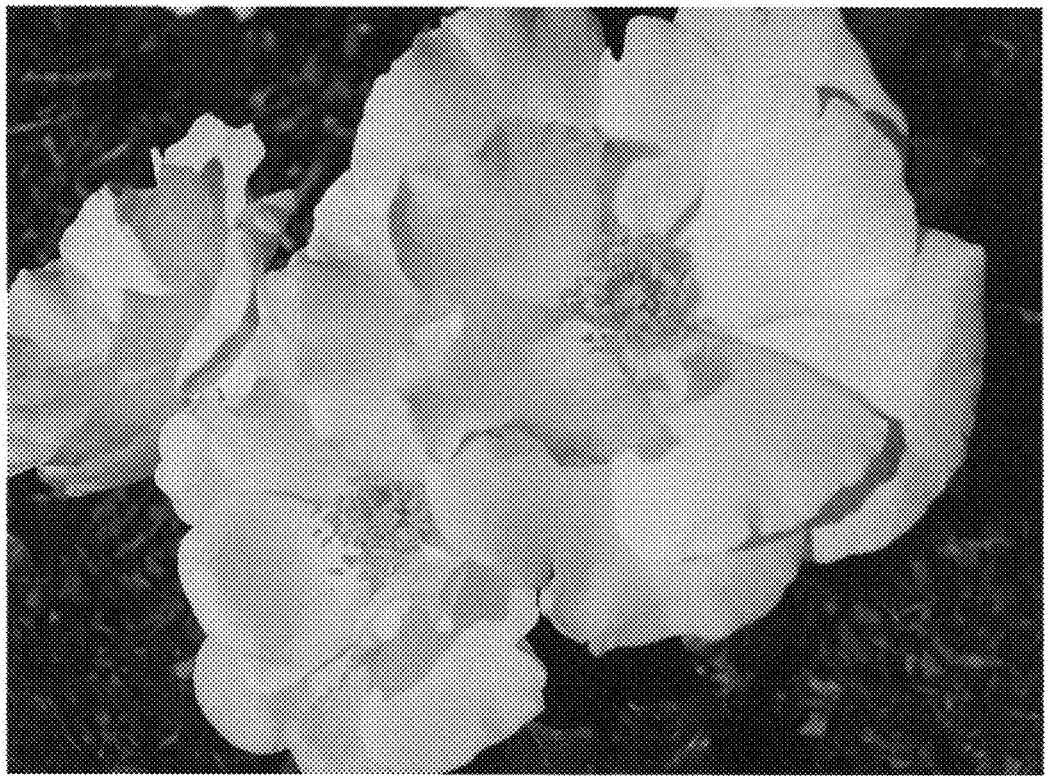

* * * * *